United States Patent [19]

Adrezin et al.

[11] Patent Number: 5,511,571
[45] Date of Patent: Apr. 30, 1996

[54] METHOD AND APPARATUS FOR GAIT MEASUREMENT

[76] Inventors: Ronald S. Adrezin, P.O. Box 788, Pocono Summit, Pa. 18346-0788; Marc A. Cordaro, 62 Oakwood Ave., Sudbury, Mass. 01775; Fikre S. Wang, 10800 Georgia Ave., Apt. 202, Wheaton, Md. 20902; Avital Fast, 162 Brookville Rd., Brookville, N.Y. 11545

[21] Appl. No.: 149,214

[22] Filed: Nov. 5, 1993

[51] Int. Cl.$^6$ ..................................................... A61H 3/00
[52] U.S. Cl. ............................ 135/66; 135/67; 73/379.08; 364/558; 364/508
[58] Field of Search ............................ 135/911, 66 OR, 135/67; 280/87.021; 73/379.01, 379.08; 364/558, 508

[56] References Cited

U.S. PATENT DOCUMENTS

| 3,517,677 | 6/1970 | Smith | 135/67 |
| 4,501,148 | 2/1985 | Nicholas et al. | 73/379.08 |
| 5,020,560 | 6/1991 | Turbeville | 135/67 |
| 5,052,375 | 10/1991 | Stark et al. | 73/379.08 X |
| 5,167,597 | 12/1992 | David | 482/68 |
| 5,172,715 | 12/1992 | Webb | 135/67 |
| 5,186,062 | 2/1993 | Roost | 73/379.08 X |
| 5,275,187 | 1/1994 | Davis | 135/67 |
| 5,339,853 | 8/1994 | Sokolis et al. | 135/67 |
| 5,368,546 | 11/1994 | Stark et al. | 364/413.02 X |

OTHER PUBLICATIONS

"Method for Recording Time, Magnitude & Orientation of Forces Applied to Walking Sticks," A. H. Seireg, M. P. Murray, & R. C. Sholz, Amer. Jrn. PhysMed. Dec. 1968.
"A Survey of time, Magnitude & Orientation of Forces Applied to Walking Sticks by Disabled Men," M. P. Murray, A. H. Seireg, R. C. Scholz, Amer. Jrn. Phys.Med. Feb. 1969.
"Cane for Measurement & Recording of Stress," H. S. Robinson, Archives of Physical Medicine & Rehabilitation, 1969.
"The Clinical Measurement & Control of Corrective & Supportive Forces," G. V. B. Cochran, Clinical Orthopaedics & Related Research, No. 75, Mar.–Apr., 1971.
"Force Measurement Device for Canes and Crutches," G. V. B. Cochran, R. Gand, and B. Blossom, Archives of Phys. Med. and Rehabilitation, vol. 54, p. 43, Jan., 1973.
"Weight Distribution and Weight–Shifting Activity During Standing Posture," M. P. Murray and R. M. Peterson, Physical Therapy, vol. 53, Mo. 7, p. 741, Jul., 1973.
"Biomechanics of Crutch Locomotion," T. E. Shoup, L. S. Fletcher and B. R. Merrill, Journal of Biomechanics, 1974, vol. 7, pp. 11–19.
"Clinical Evaluation Of A Sensory Feedback Device: The Limb Load Monitor," G. Wannstedt, R. L. Craik, Bulletin of Prosthetics Research—Spring 1978.
"Limb–Load Alarm Device For Partial–Weight–Bearing Walking Exercise," S. Miyazaki, H. Iwakura, Medical & Biological Engineering & Computing, Sep., 1978.
"One Leg Swing Through Gait Using Two Crutches," J. Stallard, E. Dounis, R. E. Major & G. K. Rose, Acta Orthop. Scand. 51, 71–77, 1980.
"Dynamic Body Forces On Axillary Crutch Walkers During Swing–Through Gait," J. F. Wilson and J. A. Gilbert, Amer. Jrn. of Phys Med., 1982 vol. 61, No. 2.

(List continued on next page.)

*Primary Examiner*—Wynn E. Wood
*Attorney, Agent, or Firm*—Steven J. Rizzi

[57] ABSTRACT

A method and apparatus for gait measurement in which a walking aid such as a walker, cane, or crutch is instrumented with load sensors to measure the loads in the aid as it is being used. The measured loads are used to analyze the user's gait to insure proper selection and sizing of a walking aid, stability of the user, and proper limb loading. In a preferred embodiment, strain gauges are mounted on the legs of a walker and connected through a signal processing interface to a computer for data analysis and display. The gauges are mounted, calibrated, and connected to the signal processing interface so as to permit measurement of the axial, bending, and torsional forces in each leg of the walker as it is being used. This data is then used for qualitative and quantitative assessment of the user's gait.

20 Claims, 3 Drawing Sheets

OTHER PUBLICATIONS

"Biofeedback Therapy to Achieve Symm. Gait In Children With Hemiplegic Cerebral Palsy: Long–Term Efficacy", B. R. Seeger, D. J. Caudrey, Arch Phys Med & Rehab, vol. 64, Apr. 1983.

"Foot–Ground Pressure Pattern Of Standing Hemiplegic Patients," R. Dickstein, M. Nissan, T. Pillar, and D. Scheer, Physical Therapy, vol. 64, No. 1, Jan., 1984.

"Portable Limb–Load Monitor Utilizing A Thin Capacitive Transducer," S. Miyazaki, et al., Journal of Biomedical Engineering, 1986, vol. 8, Jan., 1986.

"Postural Sway Biofeedback: Its Effect on Reestablishing Stance Stability in Hemiplegic Patients", A. Shumway–Cook, et al., Arch of Phys Med & Rehab, vol. 69, Jun., 1988.

"Effect Of Alterning Handle Position Of A Rolling Walker On Gait In Children With Cerebral Palsy," P. K. Levangie, et al., Physical Therapy, vol. 69, No. 2, Feb. 1989.

"Biofeedback Device For Patients On Axillary Crutches," E. J. Ang, J. C. H. Goh, K. Bost, S. L. Toh, A. Choo, Arch of Phys Medicine and Rehab., vol. 70, Aug., 1989.

"Walking Frames," G. Mulley, British Medical Journal, vol. 300, Apr., 1990.

"The Intel. Walker: A Potential Aid Hip Fracture Patient Rehab." G. K. Seidel, M.D., R. W. Soutas–Little, PhD.Archives of Phys.Med & Rehab. vol. 72 #10 1991, pp. 836–837.

"Instrumentation & Computer Interfacing Of A Standard Walker To Study User–Walker Interaction Dynamics," R. S. Adrezin, et al. BED–vol. 22, Adv in Bioengin. ASME 1992.

"A Finite Element Model Of A Walker And Its Comparison To An Instrumented Walker," R. S. Adrezin, M. A. Cordaro, F. S. Wang, A Fast, J. Ramis, BED–vol. 26, 1993, pp. 583–586.

"Walker User Risk Index: A Method for Quantifying Stability in Walker Users," R. D. Pardo, A. B. Deathe, D. A. Winter, 1993, Amer. Jrn. Physical Med. & Rehab. pp. 301–305.

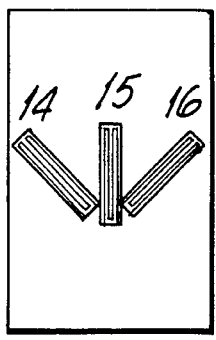 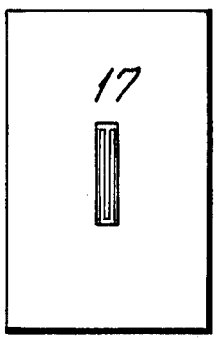 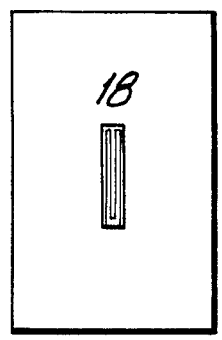 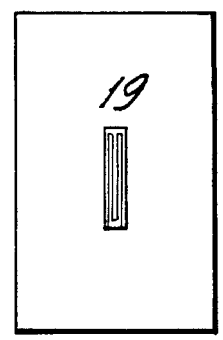
FIG. 3a    FIG. 3b    FIG. 3c    FIG. 3d
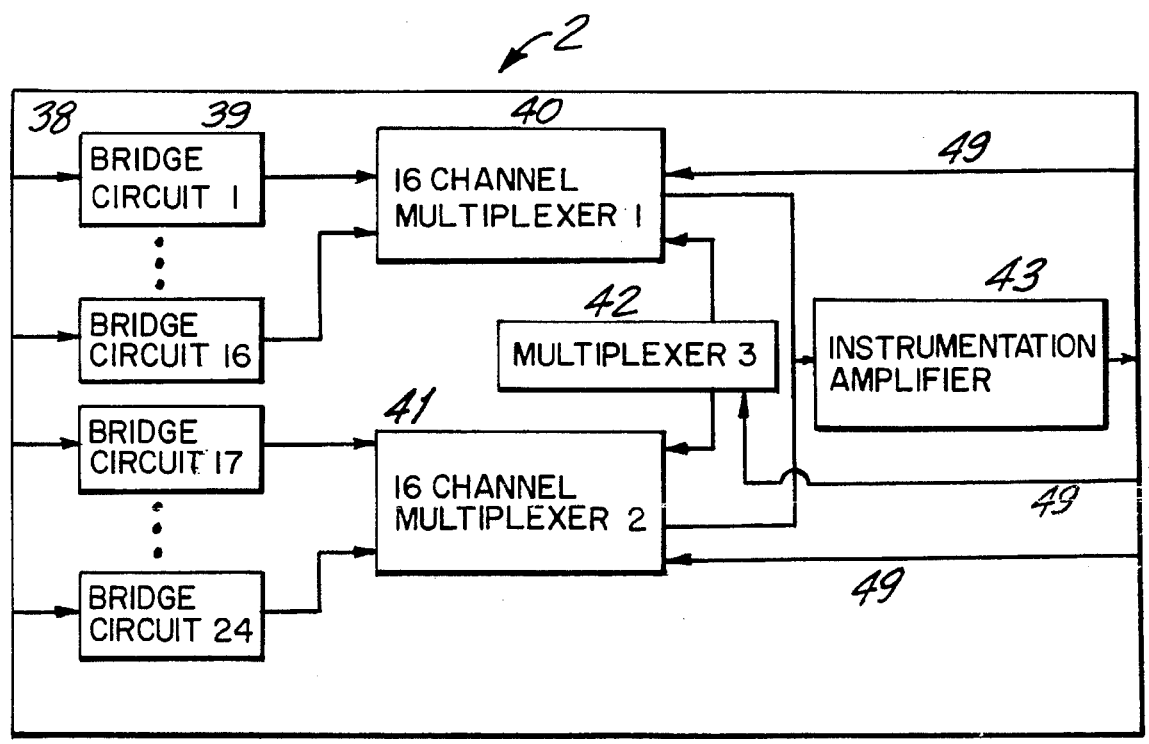
FIG. 4

METHOD AND APPARATUS FOR GAIT MEASUREMENT

FIELD OF THE INVENTION

This invention relates generally to the principle of using data related to the forces exerted on a walking aid by a user to assist in the medical evaluation and treatment of the user. In particular, this invention relates to a system and method for aiding the treatment of these patients by measuring the loads in the walking aid being used by the patient and using this data to analyze and correct any deficiencies in the person's gait.

BACKGROUND OF THE INVENTION

Generally, walking aids may be used in any instance where an individual's ability to ambulate normally has been impaired or decreased. Many people, including the elderly, use a walking aid. Such users often consist of patients suffering from injuries or other disabilities that affect their lower extremities, including the legs and feet. For example, in the instance where an individual has suffered a leg injury, therapy is often required to retrain the person to walk properly. Patients with various disabilities, such as those who have suffered from a stroke, amputations, deconditioning, and Parkinson's disease, often have difficulty walking following the onset of illness and must use a walker or other walking aid. Similarly, many patients with fractured lower extremities and other injuries require the use of walking aids during their recovery phase. Numerous types of walking aids of varied designs are available and utilized for the treatment of these and many other pathological conditions. Examples of such devices may be found in U.S. Pat. Nos. 3,517,677, 5,020,560, 5,167,597, and 5,172,715.

During these instances, and in many cases permanently, a walking aid is required to assist the patient to walk safely. In order to ensure maximum freedom and safety, and track the user's physical condition and progress in using the walking aid, it is necessary to evaluate the user's gait both qualitatively and quantitatively. Therefore, in order to aid patients with disabilities in the rehabilitation process and to allow them to stand and walk in a stable manner, it is necessary to be able to monitor their dynamic gait performance and correct any deficiencies detected. Also, measurement of the user's performance with the walking aid is necessary to assure that patients remain stable not just while walking but also when reaching for objects, transitioning from standing to sitting positions, and in other situations encountered in daily life. It is also important to know the weight distribution between the individual and the walking aid to determine if the user is leaning too far backwards and therefore might fall.

In addition, patients with lower extremities fractures are commonly instructed by their physicians to use a walking aid and bear only a certain percentage of their weight on the fractured lower extremity. Too much weight can cause further injury and too little weight can slow the healing process. A typical current practice calls for instructing the patient to stand on two scales, one beneath each leg, and learn to shift his/her body weight to reduce the load on the injured leg to within the prescribed range. However, this static teaching technique does not work well when the patient begins to walk and cannot sense the weight distribution.

There is thus a need to monitor a person's dynamic gait while using a walking aid. This is commonly done by having a therapist assist the user of the walking aid and monitor his/her performance. This method, however, provides for only limited qualitative analysis and no quantitative analysis of a person's gait.

Several gait measurement techniques of limited utility are known. For example, devices have been developed to determine the dynamic loads exerted on patients using crutches at the crutch handles and axilla as described in Wilson, et. al. The device uses force plate type transducers and other stationary sensor systems to indirectly measure the forces. However, this system is not capable of measuring dynamic gait performance. In addition, load cells have been used to study the forces exerted on a crutch, but this approach has many drawbacks. The crutch must be cut apart in order to place the cell in the crutch which alters the construction of the crutch. In addition, load cells can only measure either axial or bending forces, but not both simultaneously. Furthermore, an appropriate load cell for this application is too heavy to mount in the crutch because it will alter the crutch's characteristics by changing the weight and balance.

None of the known devices and techniques are capable of adequately measuring the dynamic gait performance of the user/patient. One problem is that there is no reliable way to measure the stability of a person using a walking aid. Often while a patient may successfully use a walking aid during normal ambulation, a fall may occur while reaching for an item on a shelf or opening a door. The standard method for the evaluation of an individual using a patient aid is by subjective observation by a physician or therapist (clinician). Stability determinations, however, require quantitative measurements, which obviously cannot be determined in this manner.

There is thus a need for walking aids that provide biofeedback to the patient in order to assist the patient in proper use of the device.

There is further need for walking aids that can be interfaced to an electronic or computer system to quantitatively define the deficiencies in ambulation and gait.

There is a further need to track patient progress through defined parameters such as stability and the percentage of body weight borne by the walker so as to insure proper rehabilitation and recovery.

SUMMARY OF THE INVENTION

The primary object of the invention is to provide a method and apparatus for measuring the gait of a patient using a walking aid.

It is a further object of the invention to provide a method and apparatus for measuring the loads in a walking aid being used by a patient.

It is a further object of the invention to provide a method and apparatus for measuring the limb loads in a patient using a walking aid.

It is a further object of the invention to provide a method and apparatus for assisting in the selection and configuration of a walking aid for a patient.

It is a further object of the invention to provide biofeedback to the user of a walking aid to instruct the user on proper use of the aid.

It is a further object of the invention to detect and indicate to the user of a walking aid that too much or too little weight is being placed on a particular extremity.

It is a further object of the invention to detect and indicate whether the patient using the walking aid is doing so in a stable manner.

It is a further object of the invention to provide a system that can monitor the loading of a walking aid with respect to time as it is being used.

The present invention achieves these and other objects and overcomes the disadvantages associated with existing gait measurement devices and techniques. A standard walking aid such as a walker, crutch, or cane, is instrumented with at least one load sensor. These sensors detect, either directly or indirectly, stresses and forces within the device as it is being used by the patient. The sensor outputs are transmitted to a signal processor and then to a data processor. Signals from the signal processor are converted to load data by the data processor and displayed on a display device in order to quantitatively and qualitatively measure the gait performance of the patient. The data may also be used to generate visual or audible signals to indicate to the user if the walking aid is being used properly.

BRIEF DESCRIPTION OF THE DRAWINGS

FIG. 3 is a view of the four quadrants of the outer diameter of a section of the leg of a walker showing the locations of the strain gauges mounted thereon.

FIG. 4 is a block diagram of the signal processing interface board used in the preferred embodiment.

DETAILED DESCRIPTION OF THE PREFERRED EMBODIMENT

Figure 1:
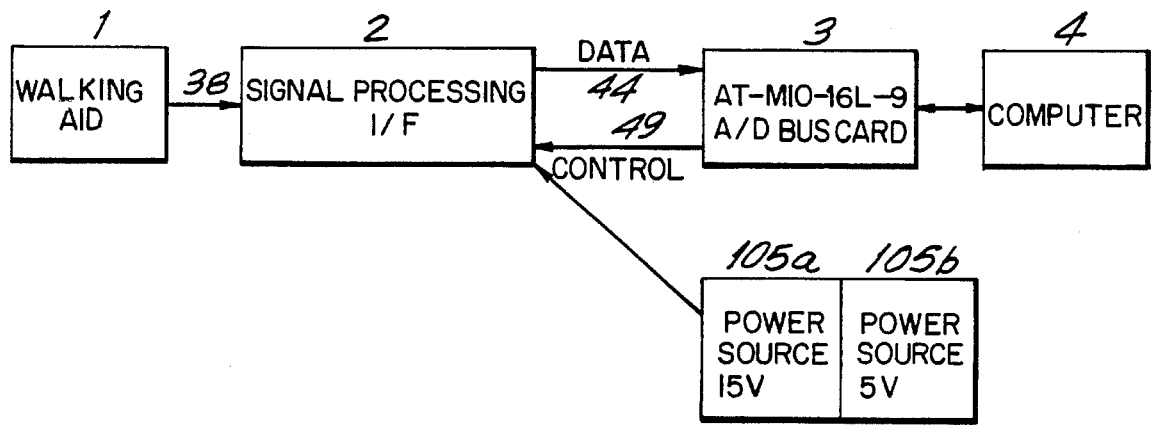
FIG. 1 is a block diagram of the preferred embodiment of the system showing a walking aid instrumented with strain gauges, a signal processing interface board, a bus card, a computer, and a power supply.

FIG. 1 shows the system block diagram of the preferred embodiment of the gait measurement apparatus and method claimed herein. In FIG. 1, a walking aid 1 instrumented with strain gauges is electrically connected to an interface board 2. Board 2 processes the resistance values of the strain gauges which are representative of the loads in the walking aid 1. After processing by interface board 2, the signals are routed to A/D bus card 3 which is resident in computer 4. A/D Bus card 3 performs analog to digital conversion of signals from board 2 and transmits digital control signals from computer 4 to board 2. Computer 4 performs data processing and display functions. Power supply 105 supplies power to interface board 2.

Figure 2:
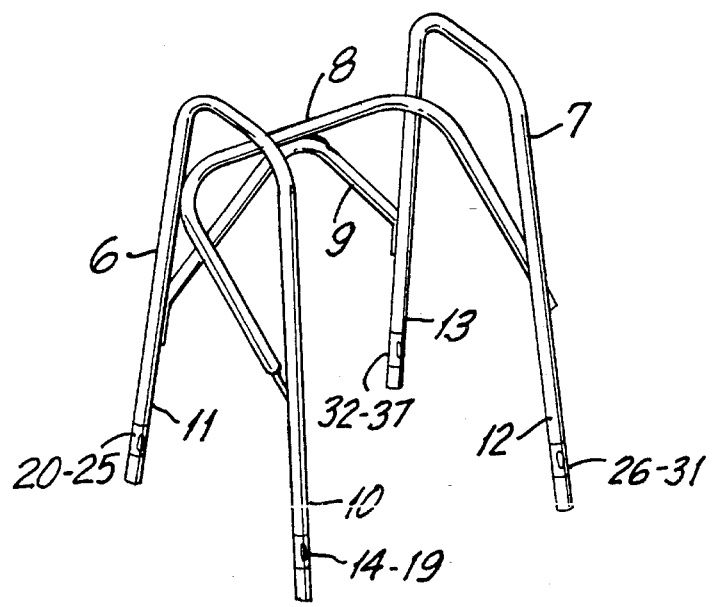
FIG. 2 is a diagram of a walker showing the mounting locations of twenty-four strain gauges.

The elements of the system will now be described in detail. FIG. 2 shows a walking device instrumented with strain gauges. A standard, aluminum walker constructed from 1 inch outer diameter thin wall tubing is shown for illustrative purposes. It will be understood by those skilled in the art that alternative types of walking aids, e.g., a cane or crutch as well as alternative constructions of such walking aids, may be similarly instrumented without departing from the spirit of the invention claimed herein. The walker 1 is constructed of side members 6 and 7, and cross members 8 and 9. Side member 6 forms legs 10 and 11 and side tube 7 forms legs 12 and 13.

The walker shown in FIG. 2 is instrumented with twenty-four strain gauges (14–37). The strain gauges may be placed in any configuration on the walker depending on the particular clinical application and corresponding measurements required. In order to measure the axial, bending and torsional forces on each leg, the preferred mounting scheme illustrated in FIGS. 3(a)–(d) was developed. FIG. 3(a)–(d) illustrates a section of the outer circumference of the lower portion of leg 10 of the walker divided into four 90° quadrants. In the preferred embodiment, legs 11, 12 and 13 incorporate the same mounting scheme. FIG. 3(a) shows the front quadrant of leg 10 which faces the patient as the walker is being used. FIG. 3(b) shows the left-facing quadrant, FIG. 3(c) the rearward-facing quadrant, and FIG. 3(d) the right-facing quadrant of leg 10. As shown in FIG. 3(a), a strain gauge rosette consisting of three gauges 14, 15, and 16 is mounted on the leg of the walker below the point of attachment of cross member 8. Gauge 15 is axially mounted along the length of the leg and gauges 14 and 16 are mounted at opposite 45° angles from gauge 15. FIGS. 3(b)–3(d) show the remaining three strain gauges (17, 18, and 19) axially mounted on leg 10 in each of the other three quadrants of the circumference. Thus, a total of four axial strain gauges spaced 90° apart are mounted on each leg.

The strain gauges 14–37 are wired to an interface board 2 with a shielded cable 38. This cable should be constructed so as to minimize noise, such as by making it as short as practical. The interface board 2 is shown in FIG. 4. All functions on the interface board 2 are controlled by a computer 4 through A/D bus card 3. The interface board 2 includes one Wheatstone bridge circuit 39 for each strain gauge. The Wheatstone bridge circuits convert the resistance-reading of the strain gauge to a voltage reading. In the preferred embodiment, 24 bridge circuits are required. Utilizing a Wheatstone bridge circuit for each strain gauge permits isolation of the axial, bending (both front-to-rear and side-to-side), and torsional forces in each of the four legs from the strain gauge outputs. For example, in leg 10, the axial forces are determined by summing the outputs of the four axial gauges (15, 17, 18, and 19) and computing the mean. Front-to-rear bending in leg 10 is determined by subtracting the output of gauge 18 from that of gauge 15 to isolate bending from axial load and then computing the mean. Side-to-side bending is determined by subtracting the output of gauge 19 from that of gauge 17 to isolate bending from axial load and then computing the mean. Finally, the torsional load is determined by subtracting the output of gauge 16 from that of gauge 14.

The interface board also includes multiplexers 40–42 and an instrumentation amplifier 43. The multiplexers are controlled by the computer through control line 49. Each output from the bridge circuits is sent to one of two-16 channel multiplexers 40 and 41. Multiplexers 40 and 41 are simultaneously switched through channels 1–16 by computer 4. A third, 8 channel multiplexer 42 enables either multiplexer 41 or 42 so that only the output of one of multiplexers 41 or 42 is routed to the instrumentation amplifier 43. The multiplexers are switched through software on command from the computer 4 so that all strain gauge outputs may be read and the data accumulated in the computer 4.

After the interface board 2 has amplified the strain gauge signals, they may be transmitted through significantly longer shielded cables 44 to the A/D bus card 3 and the computer 4.

A power supply 105 is used to supply power to interface board 2. The power supply consists of a 15+ and 15− volt d.c. source 105a and a 5+ volt d.c. source 105b. Source 105a powers the integrated circuits on the board 2. Source 105b powers the strain gauges 14–37. The 5+ volt power source 105b is preferably rated at 150 microvolt rms, 1 millivolt peak to peak ripple and noise. The power source 5b should have low ripple and noise because the signals from the bridge circuits have a magnitude on the order of millivolts. This signal is amplified with a gain on the order of 500. The output from the amplifier 43 and the ground are connected with two 18 AWG wires each (biwiring) to reduce loss through the cables that connect the interface board 2 to the A/D bus card 3.

A National Instruments AT-MIO-16L-9 bus card 3 was used for analog/digital conversion. Basic data acquisition functions are accomplished with National Instruments Lab-Windows software. Signal conditioning and data acquisition procedures were written in the C programming language using LabWindows subroutines. A strain gauge is selected for reading and its output switched through the multiplexers 40–42 to the instrumentation amplifier 43. The gauges are alternately sampled at a rate of 12 Hz and the data stored in RAM.

The raw data is then digitally filtered using a low-pass Butterworth filter and signal averaging. The filtered data, indicative of the amplified voltage outputs from the Wheatstone bridge circuits 39, is converted to strain values using the calibration curves already determined for each strain gauge as discussed below. The use of calibration curves reduces the errors caused by installation of the strain gauges 14–37 and the non-uniformity of the tubes of the walker 1.

The procedures for sampling and conditioning the data are well known to those skilled in the art. It will be appreciated by those skilled in the art that any number of commercially available software packages may be used.

The strain gauges must be calibrated before initial use. This is accomplished by loading the walker with precision weights for axial, bending and torsional loads. Data is digitally filtered and averaged to reduce noise and the strain is calculated and plotted against load to obtain calibration curves for the gauges. The system is programmed to automatically "zero" each strain gauge output while the walker is unstressed. This eliminates the necessity of manually balancing each Wheatstone bridge before every use.

In addition to calibrating the strain gauges, an algorithm was developed to account for the errors in strain gauge outputs caused by the imperfect mounting of the gauges to the walker. Due to the fact that the gauges cannot be mounted perfectly along the principal axis, an additional component of strain in each axially mounted gauge is caused by a bending component in an orthogonal axis. This mounting error associated with each gauge was determined by solving the set of equations relating the total strain to the bending, axial and error components of strain for each gauge.

For example, the total strain in axially mounted strain gauge 15 is equal to the bending strain in gauge 15 plus the axial strain in gauge 15 plus an error component associated with orthogonal bending. Since four gauges 90° apart on each leg are utilized for measuring axial and bending forces, there are four equations with twelve unknowns for each leg (bending, axial, and error components of strain for each gauge). The equations are solved by making the following assumptions: 1) the axial component of strain is the same in each gauge; 2) the bending components of gauges 180° apart are equal and opposite; and 3) the orthogonal error component is linearly related to the bending component in adjacent (orthogonally mounted) gauge 17. The constant by which the two are related is determined from the calibration data. Alternatively, the orthogonal error component of gauge 15 could be related to the bending component of adjacent gauge 19 since these gauges are 180° apart and it is assumed that their bending components are equal and opposite. By making these assumptions, the system of equations is reduced to four equations and three unknowns. The linear relationship between the orthogonal error component for gauge 15 and the bending component in adjacent gauge 17 is used as a first approximation. To account for actual non-linearities and obtain a close fit of the data, a numerical iterative procedure is used. Thus, the equations are solved to obtain calculated bending and axial strains from the total strain data. This enables calculation of bending and axial stresses and, using the calibration curves for the strain gauges, the bending and axial forces.

While the walker is being used by a patient, the axial, bending, and torsional forces in the walker legs are measured and recorded. Stored in the computer 4 are relevant attributes of the patient, including weight, height, age, diagnosis, and any other desired parameters. Included in this data is the position of the legs of the walker, which are adjustable according to the height of the user. This dimension must be known because the height of the walker determines the moment arm of the legs of the walker, thereby affecting the strain measured by the gauges. A minimum of thirty seconds of data is acquired, which corresponds to several gait cycles. The force distributions in each leg of the walker are displayed to the operator of the system so as to permit the operator to quantitatively and qualitatively monitor the patient's stability and gait. In addition, data from previous trials is displayed and compared with the present data in order to monitor the patient's progress. The availability of this data also allows the operator to make decisions concerning the proper size and type of walker for the patient. It will be understood by those skilled in the art that the computer may be configured to compare any sets of parameters, produce printouts of the data, and interface with other programs, for example, spreadsheet software.

Once the loads in each leg are determined, limb load monitoring of the legs may be achieved as follows. The user of the walker is instructed to begin the gait cycle on a specified foot. Peaks in the forces in the walker legs correspond to the interval when only one foot is in contact with the ground. During this interval, the percentage of the body weight borne by the walker is determined. The remaining portion of the body weight is thus being borne by the limb in contact with the ground. In this way, dynamic limb load monitoring of each leg is accomplished. In an alternate embodiment, a sensor may be attached to the foot of the patient to detect which foot is contacting the ground. This eliminates the need to instruct the user of the walker to begin his/her gait on a specified foot.

The force data may be manipulated in many ways. Biofeedback may be provided which includes the following: the amount of weight bearing on the lower extremities and the stability of the user. This information is useful to both the user and the clinician during the user's training. For example, biofeedback may be provided to a patient who has suffered a broken leg and may only place limited weight on the leg in the form of an audible or visual signal if the patient exceeds the maximum recommended weight. Alternatively, two audible tones may be utilized, the first indicating too little loading and the second too much loading in cases where a minimum amount of force should be placed on the limb to ensure speedy recovery. In addition, a series of tones can indicate to the user the direction of the loading on the walker to alert the user to potential hazards, such as imbalance as a result of the user reaching for a doorknob or an item on a shelf.

Figure 5:
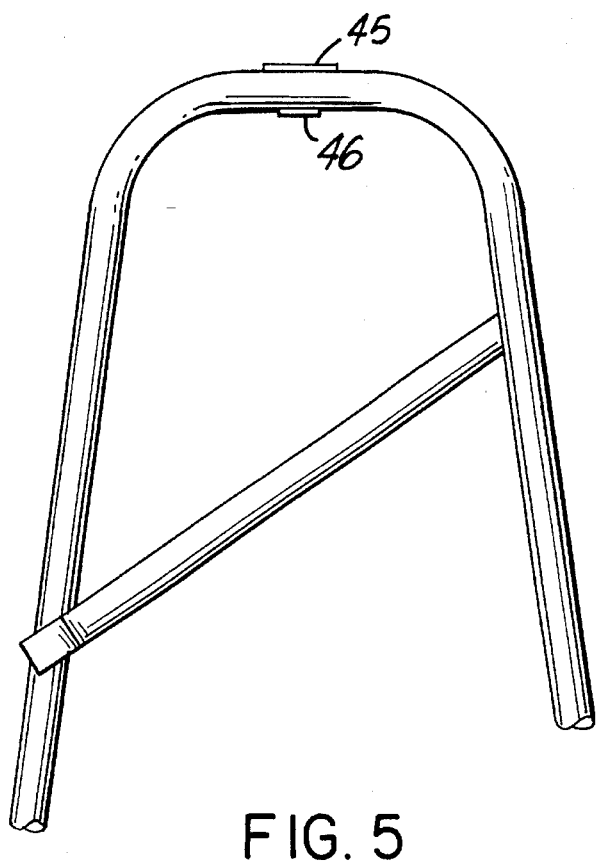
FIG. 5 shows alternate embodiments of the walker with force sensors mounted to the handles.

In certain clinical situations, it may also be desired to measure the forces exerted by the walker's user at the handles of the walker. FIG. 5 shows an enlarged side view of the handle at the top of side members 6 and 7. A sensor 45 (e.g., piezoelectric, capacitance, thin-film, load cell) is mounted on the handle. Alternatively, a strain gauge rosette 46 may be bonded to the underside of the handle.

Figure 6:
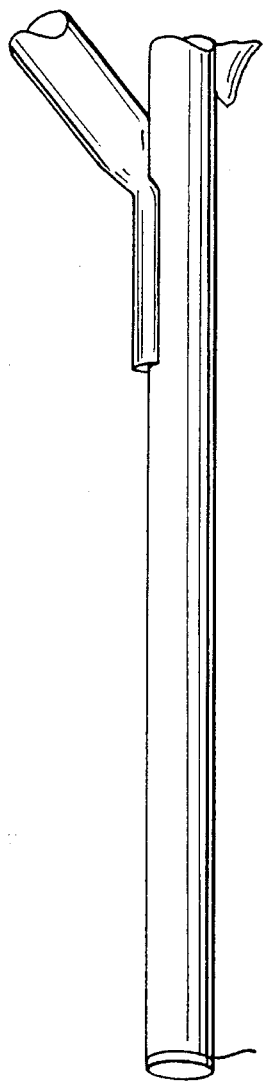
FIG. 6 is an enlarged front view of the base of a leg of the walker showing a load cell mounted to the base of the leg.

FIG. 6 shows an alternate method for measuring the axial forces at the interface between the walker legs and the floor. A load cell 47 is mounted at the bottom of the leg. The signal from the load cell is then processed similarly to those of the strain gauges.

It will be appreciated by those skilled in the art that, although strain gauges are used in the preferred embodiment, any number of force sensors may be utilized for measuring the loads in the walker, including piezoelectric, capacitance, thin-film and load cell. The quantity, location and type of sensor used is based on the static and dynamic requirements of the clinical application.

Once the data is reduced by the computer, it is displayed so as to facilitate the clinician's understanding of the stresses realized by the walker. Real-time data as well as that from previous trials can be viewed to analyze the progress of the user. Feedback may be provided both for the clinician and the walker's user.

Figure 7:
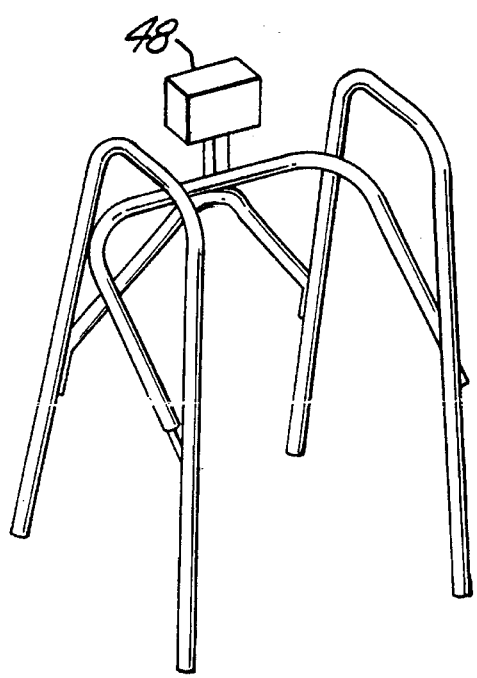
FIG. 7 shows a biofeedback module attached to the walker.

FIG. 7 shows a system where the walker 1 is interfaced with a biofeedback module 48 to provide visual and/or auditory feedback. The biofeedback module can contain all necessary signal and data processing functions and may be attached to the walker (via a cable or telemetry unit) or worn by the user. This embodiment has the advantage of a free standing system that does not hinder the mobility of the user.

It is possible to use only five strain gauges per leg consisting of a rosette and two single strain gauges mounted 120° apart on the leg. Obviously, the equations for resolving the forces in the legs to axial and bending components must be modified and the accuracy will not be as great as that of the six gauge per leg system.

Whereas the preferred form of the invention has been illustrated and described, it will be apparent to those skilled in the art that various changes and modifications may be made without deviating from the inventive concepts set forth herein.

We claim:

1. A system for measuring the gait of a person using a walker comprising:

a walker comprising a plurality of support legs and at least one handle, at least one first load sensor mounted to at least one of said support legs, said first load sensor positioned to sense at least one of the axial, bending, or torsional loads in at least one of said legs, at least one second load sensor mounted to said at least one handle, signal processing means in electrical connection with said load sensors, power supply means electrically connected to said signal processing means for supplying power to said signal processing means, data processing means connected to said signal processing means for controlling said signal processing means and processing the data from said load sensor, and data display means connected to said signal processing means for displaying the data processed by said signal processing means.

2. The system of claim 1 wherein said first load sensor is a strain gauge.

3. The system of claim 1 wherein said signal processing means, said data processing means, said power supply means, and said data display means are mounted to said walker.

4. The system of claim 2 wherein:

said walker comprises four legs, each of said legs is instrumented with at least two axially mounted strain gauges for sensing the axial loads in said legs.

5. The system of claim 4 wherein:

each of said legs is instrumented with at least two axially mounted strain gauges for sensing bending loads in said legs.

6. The system of claim 4 wherein:

each of said legs is further instrumented with two strain gauges mounted adjacent to and at opposite 45° angles from one of said axially mounted strain gauges for sensing the torsional loads in said legs.

7. An instrumented walker system comprising:

a walker having a plurality of support legs and at least one handle, a plurality of load sensors mounted to each of said legs, a signal processing interface electrically connected to said load sensors, a power supply electrically connected to said interface, a computer connected to said interface for controlling said signal processing interface and processing the data from said load sensors, said computer having a display for displaying said processed data, wherein said signal processing interface, said power supply, and said computer are mounted on said walker.

8. The system of claim 7 wherein said plurality of strain gauges are positioned so as to sense the axial, front-to-rear bending, side-to-side bending, and torsional loads in each of said legs.

9. A method for making gait measurements on a person using a walker, the method comprising:

mounting at least one first load sensor to said walker, said first load sensor positioned to sense at least one of the axial, bending, or torsional loads in said walker and capable of supplying an electrical output signal, mounting at least one second load sensor to said at least one handle, said second load sensor capable of supplying an electrical output signal, detecting the output signals from said load sensors, transmitting said output signals to a signal processing means, processing said signals for communication to a data processing means, converting said processed signals to values representative of the load sensed by said load sensor, and displaying said load values.

10. The method of claim 9 wherein said first load sensor is a strain gauge.

11. The system of claim 1 wherein said second load sensor is positioned to sense at least one of the axial, bending, or torsional loads in said handle.

12. The system of claim 8 further comprising an alarm for alerting the user that the walker is imbalanced.

13. The system of claim 8 further comprising an alarm for alerting the user that too much weight is being borne by a limb.

14. The system of claim 8 further comprising an alarm for alerting the user that additional weight should be borne on a designated limb.

15. The system of claim 12 wherein said alarm is an audible alarm.

16. The system of claim 13 wherein said alarm is an audible alarm.

17. The system of claim 14 wherein said alarm is an audible alarm.

18. An instrumented walker system comprising:

a walker having a plurality of support legs and at least one handle, at least six strain gauges mounted to each of said plurality of legs, said at least six strain gauges comprising three axially mounted strain gauges and a strain gauge rosette, said axial gauges and said rosette spaced 90° apart, wherein said rosette comprises an axial mounted strain gauge and two strain gauges mounted adjacent to and at opposite 45° angles from said axial strain gauge, a signal processing interface electrically connected to said strain gauges, said interface comprising a Wheatstone bridge circuit for each strain gauge, a power supply electrically connected to said interface, a computer connected to said interface for controlling said signal processing interface and processing the data from said strain gauges, said computer having a display means for displaying said processed data.

19. The system of claim 18 wherein said strain gauges are positioned to sense the axial, front-to-rear bending, side-to-side bending, and torsional loads in each of said legs.

20. The system of claim 7 wherein said load sensors comprise strain gauges.

* * * * *